United States Patent [19]

Bogdanowicz, Jr.

[11] B 4,013,649

[45] Mar. 22, 1977

[54] METHOD OF MAKING 4-AMINO-6-T-BUTYL-3-MERCAPTO-1,2,4-TRIAZIN-5-ONE

[75] Inventor: Mitchell Joseph Bogdanowicz, Jr., Spencerport, N.Y.

[73] Assignee: E. I. Du Pont de Nemours and Company, Wilmington, Del.

[22] Filed: Oct. 11, 1974

[21] Appl. No.: 514,259

[44] Published under the second Trial Voluntary Protest Program on March 23, 1976 as document No. B 514,259.

Related U.S. Application Data

[63] Continuation-in-part of Ser. No. 385,750, Aug. 6, 1973, abandoned.

[52] U.S. Cl. .................... 260/248 AS; 260/455 R; 260/487; 260/561 HL; 260/502.6; 260/546; 260/544 Y; 260/539 R; 260/295 S

[51] Int. Cl.$^2$ ...................................... C07D 253/06

[58] Field of Search ............................. 260/248 AS

[56] References Cited

UNITED STATES PATENTS 3,544,570  12/1970  Timmler et al. ................. 260/248

*Primary Examiner*—John M. Ford

[57] ABSTRACT

Method of making 4-amino-6-t-butyl-3-mercapto-1,2,4-triazin-5-one comprising halogenating a 3,3-dimethylbutyric acid with $Br_2$ or $Cl_2$ to produce a 2,2-dihalo-3,3-dimethylbutyric acid then reacting the latter with thiocarbohydrazide. Alternatively, a 3,3-dimethylbutyryl chloride can be used as starting material, in which case the halogenation product is contacted with water, an aqueous base, an alcohol, a mercaptan, or an amine to convert it to an acid or salt thereof, anhydride, ester, thioester or amide, and the latter is reacted with thiocarbohydrazide.

9 Claims, No Drawings

METHOD OF MAKING 4-AMINO-6-T-BUTYL-3-MERCAPTO-1,2,4-TRIAZIN-5-ONE

CROSS-REFERENCE TO RELATED APPLICATION

This application is a continuation-in-part of Applicant's copending application, Ser. No. 385,750, filed Aug. 6, 1973, now abandoned.

BACKGROUND

The compound 4-amino-6-t-butyl-3-methylthio-1,2,4-triazin-5-one is a commercial herbicide. It is made as disclosed generally in Westphal et al., U.S. Pat. No. 3,671,523, issued June 20, 1972, by reaction of methyl iodide with 4-amino-6-t-butyl-3-mercapto-1,2,4-triazin-5-one. The latter compound can be made, as also disclosed generally in U.S. Pat. No. 3,671,523, by reacting t-butylglyoxylic acid with thiocarbohydrazide. The t-butylglyoxylic acid is made by oxidation of pinacolone, which is costly on a manufacturing scale.

German Offenlegungsschrift No. 2,003,144, published July 29, 1971, discloses an alternative process for producing 4-amino-6-t-butyl-3-mercapto-1,2,4-triazin-5-one which can be represented as follows:

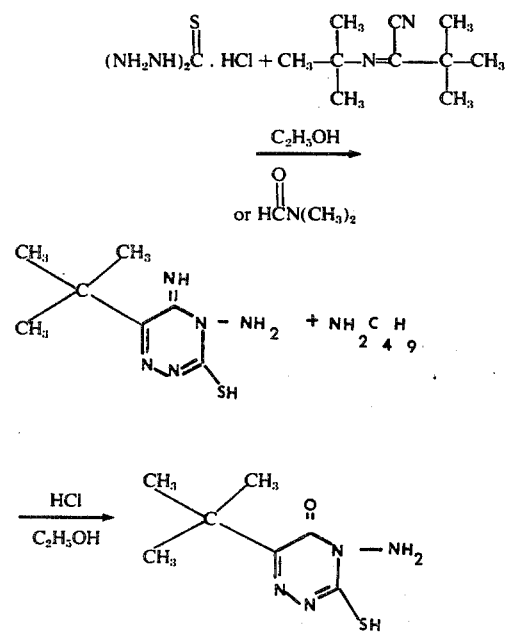

The present invention provides another alternative route for producing 4-amino-6-t-butyl-3-mercapto-1,2,4-triazin-5-one.

One step of the process of this invention involves bromination or chlorination of 3,3-dimethylbutyric acid to produce novel 2,2-dihalo-3,3-dimethylbutyric acids. Bromination and chlorination of acetic and propionic acids are described in French Pat. No. 1,241,836 (1960) and British Pat. No. 752,761 (1956).

SUMMARY

This invention is a process for making 4-amino-6-t-butyl-3-mercapto-1,2,4-triazin-5-one which comprises:

a. reacting a compound of the formula:

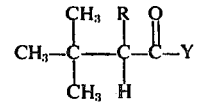

where
R is H, Br or Cl and
Y is Cl, Br or OH;
with $Br_2$ or $Cl_2$, in the presence of a catalyst when Y is OH, to produce a compound of the formula:

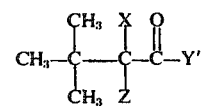

where X and Z are each independently Cl or Br, and Y' is Cl or Br; then, contacting the compound with a compound selected from $R^1OH$, $R^1SH$ and $R^2R^3NH$, where
$R^1$ is H, $C_1$–$C_4$ alkyl, phenyl or benzyl, an alkali metal cation, or an alkaline earth metal cation, and $R^2$ and $R^3$ are each independently H, $C_1$–$C_4$ alkyl, phenyl or benzyl,
to form a compound of the formula:

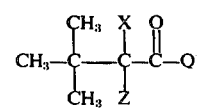

where Q is $-OR^1$, $SR^1$, $-NR^2R^3$ or

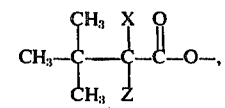

then
b. reacting the product of step a. with thiocarbohydrazide in a polar solvent.

The invention includes, as novel compounds, the intermediates of formulae II and III above, which can be represented by the general formula:

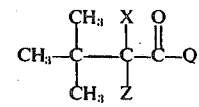

where
Q' is Cl or Q as defined above, and
X and Z are as defined above.

DESCRIPTION

The process of this invention can be represented schematically as follows:

Step a.

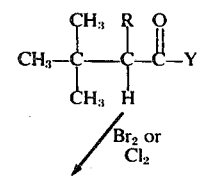

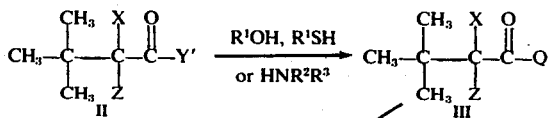

Step b.

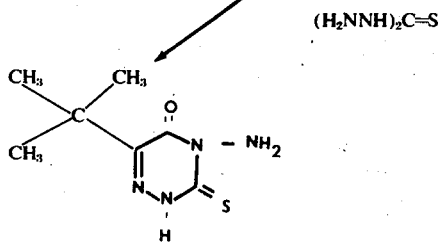

where
R = H, Br or Cl;
Y = Cl, Br or OH;
Y' = Cl, or Br;
X = Br or Cl;
Z = Br or Cl;
R¹ = H, alkyl, aryl, aralkyl, alkali metal ion or alkaline earth metal ion;
R² and R³ = hydrogen, alkyl, aryl or aralkyl;
Q = —OR¹, —SR¹, NR²R³ or

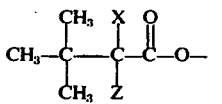

STARTING MATERIALS

Compounds of formula I where R is H and Y is OH can be made by the acid catalyzed addition of vinylidene chloride (1,1-dichloroethylene) to a tertiary butyl cation source:

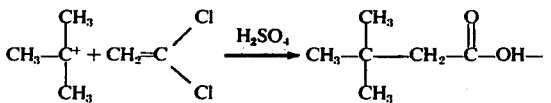

Suitable t-butyl cation sources include t-butyl chloride, t-butyl alcohol, 2-methylpropene and 1-(2,4,4-trimethyl)pentene. This reaction is described in Bott, K., Angew. Chem. Int. Ed. 4, (1965). Equimolar quantities of the t-butyl cation precursor and vinylidene chloride are added to 50 – 100% aqueous sulfuric acid containing 0 – 8% boron trifluoride. At temperatures between −20° – 80°C, the reaction proceeds in 1 – 15 hours to yield 3,3-dimethylbutyric acid upon aqueous workup. The addition of boron trifluoride (or its ether complex) is not necessary; however, it dramatically reduces the reaction time. The reaction is considered complete when the vinylidene chloride is completely consumed. This may be determined by gas chromatography.

Compounds of formula I wherein R is H and Y is Cl can be made by reacting a corresponding compound wherein Y is OH with phosphorous trichloride or phosgene at atmospheric pressure and at a temperature of 100°C.

Compounds of formula I wherein R is Br or Cl can be made by reacting a corresponding compound wherein R is H with Br₂ or Cl₂ atmospheric pressure and 50°C. For halogenation of 3,3-dimethylbutyric acid, a catalyst such as PCl₃ should be used.

Step a.

The compound of formula I is halogenated with Br₂ or Cl₂ to produce a dihalo or trihalo compound of formula II at a pressure in the range of 1 – 20 atmospheres and a temperature in the range of 75° – 200°C, preferably 1 – 5 atmospheres at 150° – 170°C. Lower pressures may require use of higher temperatures. No solvent is needed, but an inert organic solvent can be used. For halogenation of compounds wherein Y is —OH, a catalyst is used; suitable catalysts include elemental phosphorous, halides, oxyhalides, oxygen acids and oxides of phosphorous, thionyl chloride, phosgene, 3,3-dimethylbutyryl chloride, 2-halo-, and 2,2-dihalo-3,3-dimethylbutyryl halide.

Alternatively, dihalogenation can be achieved by addition of a compound of formula I to a solution of Br₂ or Cl₂ in a tertiary organic amine, such as pyridine or triethylamine, at a temperature of 0° – 50°C and a pressure of 1 – 5 atmospheres.

Before proceeding to step b, compounds of formula II wherein Y' is Cl or Br are contacted with water or aqueous base, an alcohol, a phenol, a mercaptan or an amine (i.e., a compound of the formula R¹OH, R¹SH or HNR²R³, where R¹, R² and R³ are as defined above) to yield the corresponding acid, salt, anhydride, ester, or amide of formula III. Preferably, R¹, R² and R³ are each independently hydrogen, C₁–C₄ alkyl, phenyl or benzyl. When the 2,2-dihalo-3,3-dimethylbutyryl halide is prepared by addition of Br₂ or Cl₂ to a solution of a compound of formula I in a tertiary amine, then the reaction mixture is contacted with one equivalent or more of water, the resulting product is a salt of the tertiary amine and a 2,2-dihalo-3,3-dimethylbutyric acid. The salt can be converted to the free acid by treatment with mineral acid, or it can be used directly in step b.

Step b.

The product of step a is condensed with thiocarbohydrazide in a solvent at 20° – 160°C and 1 – 5 atmospheres. The solvent can be water or any polar solvent that does not itself react with thiocarbohydrazide. An alkali metal iodide accelerates the reaction, but is not necessary. Preferred conditions are an aqueous solvent system, sodium iodide catalyst, a temperature of 50° – 100°C, and a pressure of 1 – 2 atmospheres.

EXAMPLE 1

A mixture of 100 parts 3,3-dimethyl butyric acid, 345 parts bromine and 10 parts phosphorous trichloride was heated to 150° for one hour in a bomb. The resulting solid, after in vacuo removal of excess bromine and hydrogen bromide consisted of 45% 2,2-dibromo-3,3-dimethyl butyric acid (m.p. 241° – 243°C.) and 55% 2-bromo-3,3-dimethylbutyric acid (m.p. 56° – 58°C.). The dibromo acid preferentially crystallizes from the mixture upon recrystallization in hexane.

A mixture of 2,2-dibromo-3,3-dimethylbutyric acid, 55 parts, and thiocarbohydrazide, 22 parts, in 500 parts of (1:1) methanol and water was heated to reflux for five hours. Upon cooling the reaction mixture to 0°C., a solid formed and was collected. The solid, 4-amino-6- t-butyl-3-mercapto-1,2,4-triazin-5-one, was obtained in 78% of theory (29 parts).

EXAMPLE 2

A stirred solution of 100 parts of 3,3-dimethylbutyric acid and 59 parts phosphorous trichloride was heated to 100°C. for one hour. Phosphoric acid precipitated from the resulting 3,3-dimethylbutyryl chloride solution.

Slow addition of 100 parts of 3,3-dimethylbutyryl chloride to a solution of 288 parts bromine in 500 parts pyridine at 5° – 15°C. resulted in precipitation of pyridine hydrobromide. After 2 hours, the reaction mixture was poured into 2 liters of water and extracted with methylene chloride. Evaporation of the solvent, in vacuo, resulted in 240 g., 79%, of 2,2-dibromo-3,3-dimethylbutyric acid as the pyridine salt. Recrystallization from hexane resulted in a crystalline material, m.p. 88° – 92°C.

A mixture of pyridinium 2,2-dibromo-3,3-dimethyl butyrate, 71 parts, and thiocarbohydrazide, 22 parts, in 500 parts of (1:1) methanol and water was heated to reflux for 3 hours. Upon cooling the reaction mixture to 0°C., a precipitate formed and was collected to yield 35 parts (94% of theory) of 4-amino-6-t-butyl-3-mercapto-1,2,4-triazin-5-one, m.p. 213° – 214°C.

EXAMPLE 3

A mixture of 10 parts of pyridinium 2,2-dibromo-3,3-dimethylbutyrate and 50 parts of 50% aqueous hydrochloric acid resulted in precipitation of 2,2-dibromo-3,3-dimethylbutyric acid in quantitative yield. The solid was recrystallized from butyl chloride, m.p. 241° – 243°C. It can then be reacted with thiocarbohydrazide as described in Example 1 to form 4-amino-6-t-butyl-3-mercapto-1,2,4-triazin-5-one.

I claim:

1. A method of making 4-amino-6-t-butyl-3-mercapto-1,2,4-triazin-5-one which comprises:
   a. reacting a compound of the formula:

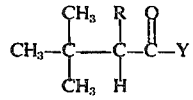    I where
R is H, Br or Cl and
Y is Cl, Br or OH;
with $Br_2$ or $Cl_2$, in the presence of a catalyst when Y is OH, to produce a compound of the formula:

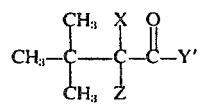    II where X and Z are each independently Cl or Br and Y' is Cl or Br; then, contacting the compound with a compound selected from $R^1OH$, $R^1SH$ and $R^2R^3NH$, where $R^1$ is H, $C_1$–$C_4$ alkyl, phenyl, benzyl,
   an alkali metal cation, or an alkaline earth metal cation, and
   $R^2$ and $R^3$ are each independently H, $C_1$–$C_4$ alkyl, phenyl or benzyl;
to form a compound of the formula:

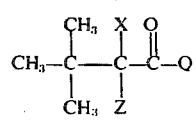    III where Q is $-OR^1$, $-SR^1$, $-NR^2R^3$ or

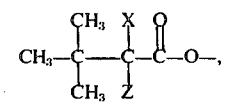

then
   b. reacting the product of step a. with thiocarbohydrazide in a polar inert solvent.

2. Method of claim 1 wherein step a. is carried out at 75° – 200°C. and 1 – 20 atmospheres and the catalyst, when Y is OH, is selected from phosphorus and its halides, oxyhalides, oxygen acids and oxides, thionyl chloride, phosgene, 3,3-dimethylbutyryl chloride, 2-halo- and 2,2-dihalo-3,3-dimethylbutyryl halide, and wherein step b. is carried out at 20° – 160°C. and 1 – 5 atmospheres.

3. Method of claim 2 wherein step a. is carried out at 150° – 170°C. and 1 – 5 atmospheres and step b. is carried out at 1 – 2 atmospheres and 50° – 100°C. in a water/alcohol medium.

4. Method of claim 3 wherein the starting material is 3,3-dimethylbutyric acid, in step a. the halogen is $Br_2$ and the catalyst is $PCl_3$, and step b. is carried out at 1 atmosphere in water/methanol.

5. Method of claim 1 wherein the starting material is 3,3-dimethylbutyryl chloride, step a. is carried out at 1 – 5 atmospheres and 0° – 50°C. in a tertiary organic amine solution, the reaction mixture is contacted with water to form the tertiary amine salt of the 2,2-dihalo-3,3-dimethylbutyric acid for use in step b. which is carried out at 20° – 160°C. and 1 – 5 atmospheres.

6. Method of claim 5 wherein in step a. the halogen is $Br_2$, the tertiary amine is pyridine, the temperature is 5° – 15°C. and the pressure is 1 atmosphere and step b is carried out at 50° – 100°C. and 1 – 2 atmospheres in water/methanol.

7. A method of making 4-amino-6-t-butyl-3-mercapto-1,2,4-triazon-5-one which comprises reacting a compound of the formula:

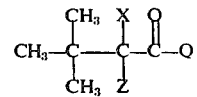

where X and Z are each independently Cl or Br and Q is $-OR^1$, $-SR^1$, $-NR^2R^3$ or

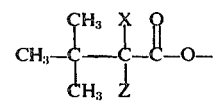

where
$R^1$ is H, $C_1$–$C_4$ alkyl, phenyl, benzyl, an alkali metal cation, or an alkaline earth metal cation, and
$R^2$ and $R^3$ are each independently H, $C_1$–$C_4$ alkyl, phenyl or benzyl;
with thiocarbohydrazide in a polar inert solvent.

8. Method of claim 7 wherein the reaction is carried out at 20° – 160°C and 1-5 atmospheres.

9. Method of claim 8 wherein the reaction is carried out at 50°–160°C and 1-2 atmospheres in a water/alcohol medium.

* * * * *